United States Patent
Henry

(10) Patent No.: US 9,028,415 B2
(45) Date of Patent: May 12, 2015

(54) BLOOD FLOW MONITOR WITH VISUAL DISPLAY

(75) Inventor: Donald A. Henry, Greensburg, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 1907 days.

(21) Appl. No.: 11/594,415

(22) Filed: Nov. 8, 2006

(65) Prior Publication Data

US 2007/0167789 A1     Jul. 19, 2007

Related U.S. Application Data

(60) Provisional application No. 60/737,333, filed on Nov. 16, 2005.

(51) Int. Cl.
| | |
|---|---|
| *A61B 8/00* | (2006.01) |
| *A61B 8/12* | (2006.01) |
| *A61B 5/026* | (2006.01) |
| *A61B 5/00* | (2006.01) |
| *A61B 8/06* | (2006.01) |

(52) U.S. Cl.
CPC . *A61B 8/12* (2013.01); *A61B 5/026* (2013.01); *A61B 5/6876* (2013.01); *A61B 5/6884* (2013.01); *A61B 8/06* (2013.01)

(58) Field of Classification Search
CPC .............................. A61B 5/026; A61B 5/6876

USPC ......... 600/453–457, 407, 473, 476, 479, 504, 600/505
See application file for complete search history.

(56) References Cited

U.S. PATENT DOCUMENTS

| | | | |
|---|---|---|---|
| 4,501,279 A | 2/1985 | Seo | A61B 10/00 |
| 5,052,395 A | 10/1991 | Burton et al. | A61B 8/00 |
| 6,251,077 B1 | 6/2001 | Mo et al. | A61B 8/06 |
| 6,554,801 B1* | 4/2003 | Steward et al. | 604/164.03 |
| 6,616,611 B1* | 9/2003 | Moehring | 600/454 |
| 6,682,483 B1* | 1/2004 | Abend et al. | 600/437 |
| 7,427,265 B1* | 9/2008 | Keilman et al. | 600/300 |
| 2007/0088214 A1* | 4/2007 | Shuros et al. | 600/437 |

* cited by examiner

*Primary Examiner* — Unsu Jung
*Assistant Examiner* — Daniel Huntley
(74) *Attorney, Agent, or Firm* — Brinks Gilson & Lione

(57) ABSTRACT

A blood flow monitor with a visual display. The monitor may include a probe monitoring circuit configured to be associated with a blood vessel. The probe monitoring circuit may transmit a burst signal and receive a reflected signal, where a frequency shift in the reflected signal represents a flow rate associated with the blood vessel. A mixer may be provided in electrical communication with the probe. A signal processing circuit in electrical communication with the output of the mixer may be configured to drive the visual display with a signal representing the flow rate associated with the blood vessel.

18 Claims, 4 Drawing Sheets

BLOOD FLOW MONITOR WITH VISUAL DISPLAY

BACKGROUND

1. Technical Field

The present invention relates to medical devices and particularly to a blood flow monitor with a visual display.

2. Background Information

The monitoring of blood flow in a vessel can be accomplished by several methods. One method uses the principle of Doppler frequency shift to measure blood flow. According to this principle, a signal reflected by a moving object will exhibit a frequency shift. The direction and degree of the frequency shift represents the direction and velocity of the moving object.

Doppler blood flow monitors typically will excite a transducer associated with a blood vessel with a short burst of ultrasonic energy. The transducer will then "listen" for a reflected signal. The difference in frequency between the original burst of energy and the reflected signal represents the velocity of the blood cells moving past the transducer. Typically, this difference is ultimately delivered to an audio speaker. By listening to the audio output of the blood flow monitor, the operator can make an assessment as to the presence of adequate blood flow in the vessel.

There are multiple shortcomings with blood flow monitors that solely have an audio output. The audio nature of the monitors limits access for persons with hearing impairments. Even for persons without a hearing impairment, every person's hearing abilities are different, particularly for low frequencies, which may make an audio output unsuitable for some persons.

Moreover, the design and manufacture of compact and portable blood flow monitors that are capable of producing very low audio frequencies is extremely difficult. In many cases, the small speakers used with portable monitors have a frequency response starting at 100 Hz, which prevents any audible indication of blood flow for low flow rates.

Additionally, the ability to detect lower velocities (and the resultant lower frequency shift) is extremely important, particularly for large blood vessels. With large vessels, the flow rate may be less to deliver the same quantity of blood compared with a smaller vessel. For example, the actual amount of blood flowing, at some given velocity, is quite different in a 1 mm vessel as compared to a 4 mm vessel.

Therefore, there is a need for a blood flow monitor that is capable of indicating a flow rate in a non-audible manner.

BRIEF SUMMARY

In one aspect, this invention provides a blood flow monitor with a visual display. The monitor may include a probe monitoring circuit configured to be associated with a blood vessel. The probe monitoring circuit may transmit a burst signal and receive a reflected signal, where a frequency shift in the reflected signal represents a flow rate associated with the blood vessel. A mixer may be provided in electrical communication with the probe monitoring circuit. A signal processing circuit in electrical communication with the output of the mixer may be configured to drive the visual display with a signal representing the flow rate associated with the blood vessel.

In another aspect, the invention provides a signal processing circuit. The circuit may include an input channel configured to receive an input signal representing a flow rate through a blood vessel. An output channel configured to output an output signal may be provided. The signal processing circuit may include a scaling logic connected between the input channel and the output channel, where the scaling logic is configured to generate a scaled signal capable of driving a visual display with the flow rate associated with the blood vessel.

According to a further aspect, the invention provides a method of monitoring the blood flow rate through a blood vessel. The method includes the step of transmitting a burst signal proximate to a blood vessel. A reflected signal is received, where a frequency shift in the reflected signal represents a flow rate associated with the blood vessel. The method includes the step of driving a visual display with the flow rate associated with the blood vessel.

DETAILED DESCRIPTION OF THE DRAWINGS AND THE PRESENTLY PREFERRED EMBODIMENTS

Figure 1:
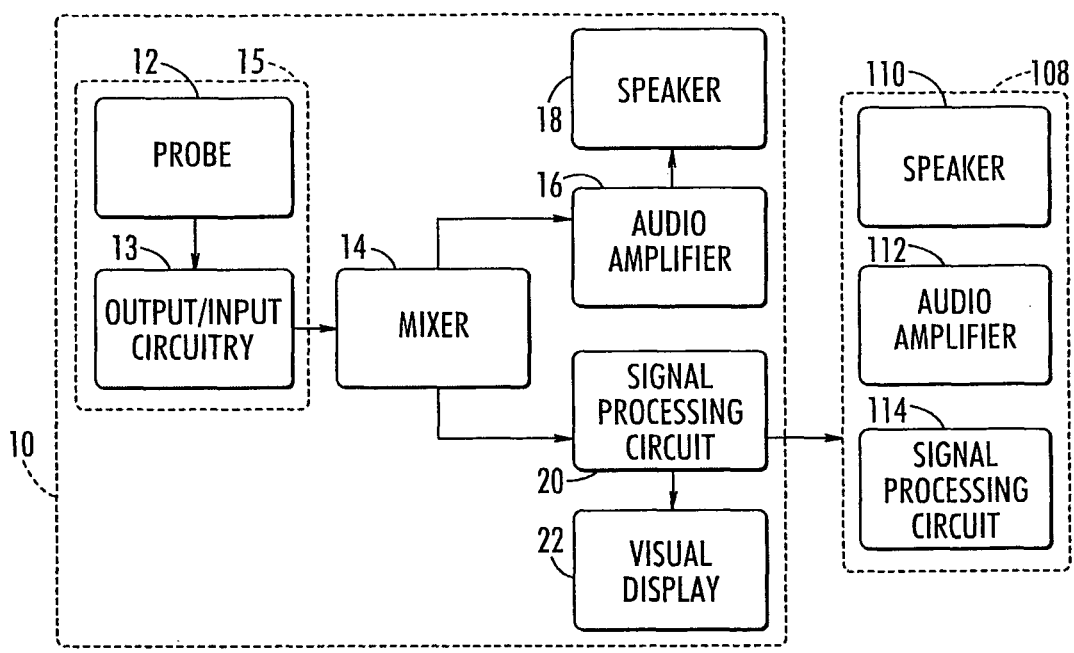
FIG. 1 is a block diagram of an example blood flow monitor.

FIG. 1 shows an example blood flow monitor 10. Although the invention will be discussed with respect to the blood flow monitor 10, the invention may be adapted for use with any device that uses the Doppler frequency shift principle to measure the speed of an object. In the example shown, the blood flow monitor 10 includes a probe monitoring circuit 15. The probe monitoring circuit has a probe 12 that may be associated with a blood vessel to be monitored. Typically, the probe 12 may be associated with a blood vessel by implanting a portion of the probe 12 in the patient such that a portion of the probe 12 contacts the blood vessel being monitored. For example, the probe 12 may include a piezoelectric crystal or other transducer that is placed directly on the blood vessel to be monitored. In other examples, the piezoelectric crystal may not directly contact the blood vessel being monitored. For example, the probe 12 may be associated with a blood vessel in a noninvasive manner.

The probe monitoring circuit 15 may measure blood flow using the principle of Doppler frequency shift. Using this principle, an original signal may be transmitted toward an object, such as blood cells, to be measured. Movement of the object will cause a frequency shift in a reflected signal. The speed and direction of the object may be determined by the degree and direction of the frequency shift.

To measure the blood flow rate, for example, the probe monitoring circuit 15 may include output/input circuitry 13 configured to transmit a burst signal at a predetermined frequency and then monitor for a reflected signal with a frequency shift. In the transmitting mode, for example, the output/input circuitry 13 may apply an ultrasonic burst signal, such as 20 MHz, to the blood vessel by exciting a piezoelectric crystal in the probe 12. After transmitting the signal, the input/output circuitry 13 may monitor for a reflected signal. For example, a piezoelectric crystal in the probe 12 may be used as a transducer by the input/output circuitry 13 to receive the reflected signal. The difference in frequency between the transmitted signal and the reflected signal is the Doppler shift. The Doppler shift represents the flow rate through the blood vessel. Typically, the greater the Doppler shift, the greater the blood flow rate. In some examples, the probe 12 may include a single piezoelectric crystal that may be used as both a transmitter and receiver; however, some embodiments contemplate that multiple piezoelectric crystals may be used. A device sold under the name Cook-Swartz Doppler Flow Probe may be a suitable probe 12 for use with the monitor 10.

The probe monitoring circuit 15 may be in electrical communication with a mixer 14. In the example shown in FIG. 1, the output/input circuitry 13 is in electrical communication with the input of the mixer 14. The mixer 14 may be configured to compare the frequency of the burst signal and the reflected signal to determine the Doppler shift. The mixer 14 may output a signal having the Doppler shift frequency. Typically, the output of the mixer 14 may be in the low microvolt range. The mixer may be implemented in hardware and/or software.

The mixer 14 may be in electrical communication with an audio amplifier 16 in some examples. The audio amplifier 16 may be configured to amplify the signal of the mixer 14 sufficiently to drive a speaker 18. The audio amplifier 16 may also be configured to process the signal received from the mixer 14. For example, the audio amplifier 16 may be configured to filter high frequency noise from the signal received from the mixer 14. In some contemplated embodiments, the audio amplifier 16 and the speaker 18 are optional.

The mixer 14 may be in electrical communication with a signal processing circuit 20. The signal processing circuit 20 may be configured to generate a signal that is capable of driving a visual display 22 with blood flow related data. The signal processing circuit 20 may be implemented in hardware and/or software. The signal processing circuit 20 may include analog components, digital components, a mix of analog and digital components, discrete logic or circuitry or a mix of discrete logic and a processor which executes instructions stored in a memory. The visual display 22 may be any device capable of visually indicating the flow rate through the blood vessel being monitored, such as an LED bar graph, an LCD bar graph, calibrated needle or numeric display. By way of another example, any display used in conjunction with a voltmeter may be suitable for visual display 22.

The signal processing circuit 20 may be configured to drive the visual display 22 with the entire flow range or a portion of the flow range. Consider a signal received by the signal processing circuit 20 having a frequency range between 0 Hz and 10 KHz, for example. In some examples, the visual display 22 may be scaled to show the entire frequency range, 0 Hz to 10 KHz. In other examples, the full scale of the visual display 22 may only include the lower portion of the frequency spectrum, such as 0 Hz to 250 Hz, which may correspond to the lower blood flow rates. If the speaker 18 were audible only above 100 Hz, for example, the full scale of the visual display 22 may be configured at 100 Hz. Accordingly, the blood flow rate corresponding to less than 100 Hz, which may not be producible in an audible manner by the speaker 18, could be perceived and monitored using the visual display 22.

The signal processing circuit 20 may also communicate with post processing logic 108. The post-processing logic 108 may include, as examples, a telemetry transmitter 110, a digital and/or analog data transmission system 112 or a monitoring system 114. The telemetry transmitter 110 may communicate with a receiver in a different vicinity than the patient. For example, blood flow rate data may be transmitted to a receiver located at a nursing station, which would allow the nurse to monitor the blood flow rate without entering the patient's room. The transmission system 112 may provide a network connection, digital or analog transmitter or other transmission circuitry and/or logic. The monitor system 114 may provide an alarm using an audible and/or visual indicator to alert the medical staff if the blood flow rate falls below a certain threshold.

Figure 2:
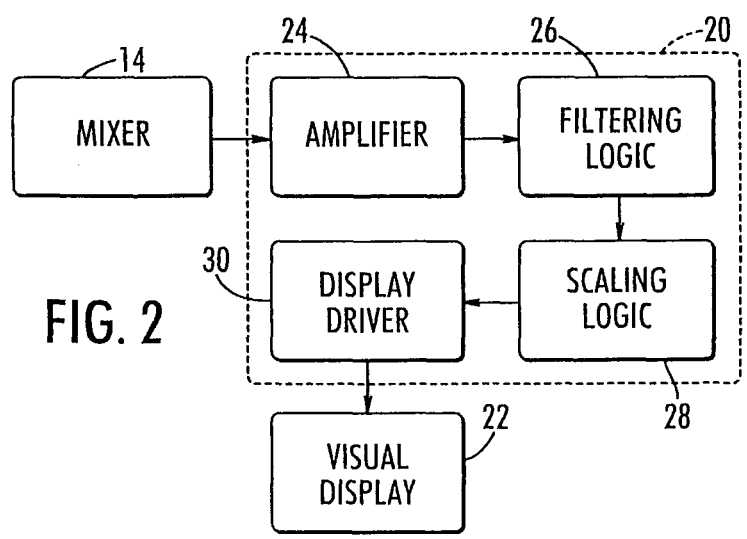
FIG. 2 is a block diagram of an example implementation of a signal processing circuit coupled to a mixer and a visual display.

FIG. 2 shows an example implementation of the signal processing circuit 20. In this example, the signal processing circuit 20 receives the output of the mixer 14 as an input to an amplifier 24. The amplifier 24 may be configured to increase the amplitude of the mixer output for further processing. In some examples, the amplifier 24 may be optional if the voltage of the signal received from the mixer 14 has sufficient amplitude for processing. The amplifier may comprise a single or multistage amplification system.

The output of the amplifier 24 is received by optional filtering logic 26. The filtering logic 26 may be used to reduce high frequency noise in the signal. The filtering logic 26 may be implemented using analog components, such as capacitors and resistors, or using digital components. Embodiments are contemplated in which filtering logic may be implemented using digital signal processing techniques, such as a finite impulse response ("FIR") filter or an infinite impulse response ("IIR") filter.

The output of the filtering logic 26 is received by scaling logic 28. The scaling logic 28 may be configured to generate a scaled signal representing the blood flow in the vessel being monitored. For example, scaling logic 28 may be configured to generate a signal indicating that the blood flow is in a certain flow range. Consider a flow rate corresponding to a Doppler frequency range of 1 Hz to 1,000 Hz, for example. Scaling logic 28 may be configured to indicate whether the signal is between 0 and 250 Hz, for example, where 250 Hz is the full scale value for the scaling logic 28. This type of bandwidth representation may be helpful where the monitor 10 includes a speaker 18. In such an example, a user may be able to hear the frequencies above 250 Hz, but be unable to clearly hear lower frequencies. In that example, the user would be able to view the visual display 22 for flow rates corresponding to frequencies below 250 Hz. The display driver 30 may be configured to drive the visual display 22 with the signal received by the scaling logic 28.

Figure 3:
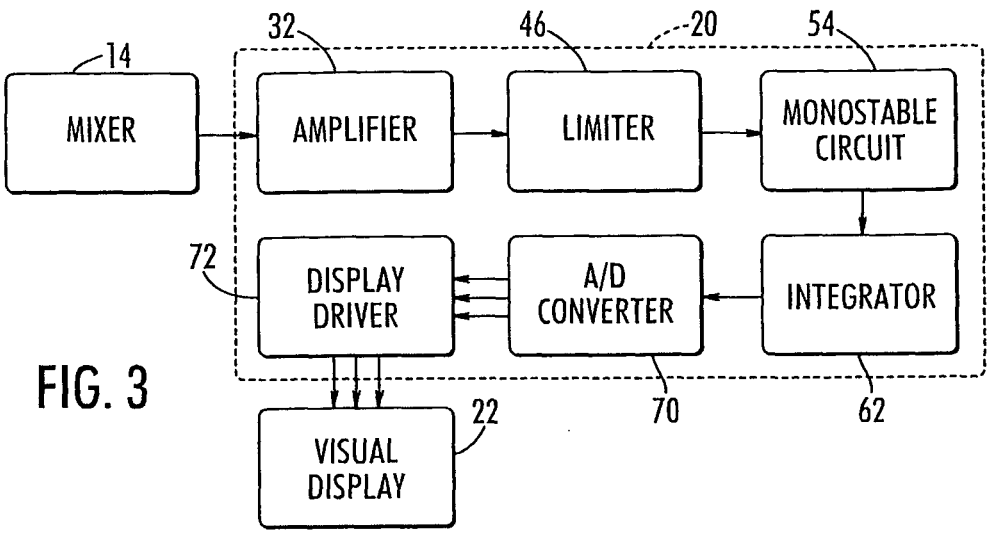
FIG. 3 is a block diagram of an example implementation of a signal processing circuit couple with a mixer and visual display.
Figure 4:
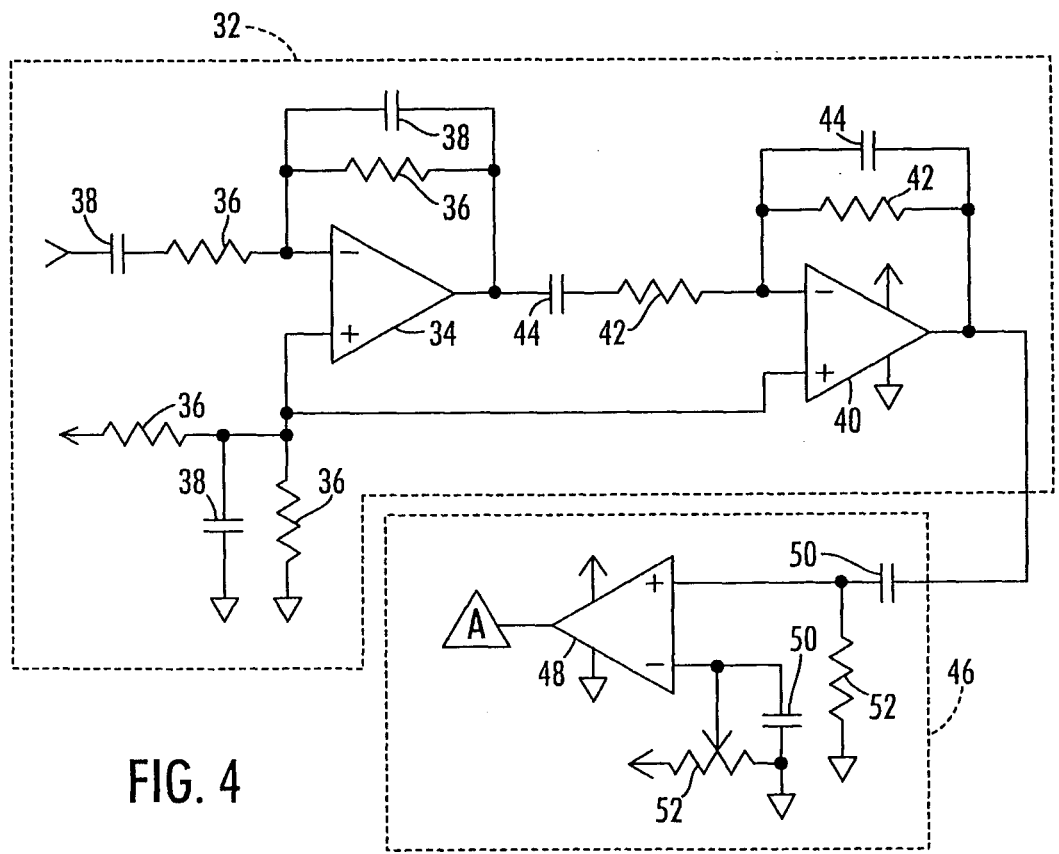
FIG. 4 is an example implementation of an amplifier and limiter that may be used in the signal processing circuit.

FIG. 3 shows an example implementation of the signal processing circuit 20. In this example, the signal processing circuit 20 includes an amplifier 32 configured to amplify the input signal received from the mixer 14. An example implementation of the amplifier 32 that may be used is shown in FIG. 4. As shown, the amplifier 32 is a two-stage amplifier. The first stage of the amplifier includes a first operational amplifier 34 with associated resistors 36 and capacitors 38. The second stage of the amplifier includes a second operational amplifier 40 with associated resistors 42 and capacitors 44. Although amplifier 32 is shown as a two-stage amplifier, the amplifier 32 could be a single stage or more than two-stage amplifier.

A limiter 46 may be connected to the output of the amplifier 32. The limiter 46 may convert the analog signal from the amplifier 32 to digital voltage levels. An example implementation of the limiter 46 is shown in FIG. 4. In this example, the limiter 46 includes an operational amplifier 48 with associated capacitors 50 and resistors 52. The limiter 46 may be configured to output a high digital voltage, such as 5 volts or 3.3 volts, when the input voltage is above a set point, while a low digital voltage, such as 0 volts, may be provided as an output when input voltage is below the set point. For example, the set point of the limiter 46 may be 0.25 volts. In this example, the output voltage of the limiter 46 would be a digital low voltage (e.g., 0 volts) except when the input signal is above 0.25 volts. At times when the input signal is above 0.25, the limiter 46 would output a digital high voltage (e.g., 5.0 volts). The set point is preferably set to as low a voltage as possible, without creating false positives from noise in the input signal.

Figure 5:
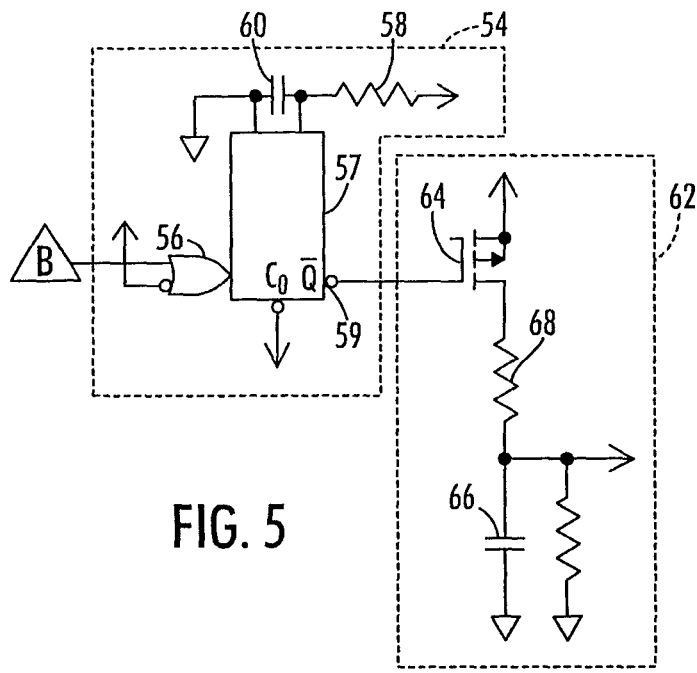
FIG. 5 is an example monostable and integrator that may be used in the signal processing circuit.

A monostable circuit 54 may be connected to the output of the limiter 46. The monostable circuit 54 is configured to generate a pulse at each rising or falling edge of the input signal. An example implementation of the monostable circuit 54 is shown in FIG. 5. The triangle A in FIG. 4 continues to the triangle B in FIG. 5. The input received from the limiter 46 is passed through an and gate 56. As shown, the and gate 56 includes an inverted input that is connected to high. The output of the and gate 56 is connected to a monostable 57. As connected, the monostable 57 is a positive edge trigger. It is also contemplated in some embodiments, however, that the monostable 57 may be triggered by a negative edge. When the output of the and gate 56 goes low, which corresponds to a rising edge of the output of the limiter 46, the output 59 of the monostable 57 will generate a pulse. The width of the pulse may be controlled by a resistor 58 and a capacitor 60.

The output of the monostable circuit 54 may be received by an integrator 62. The integrator 62 may be configured to develop a voltage that is dependent on the frequency of the signal received by the monostable circuit 54. An example implementation of the integrator 62 is shown in FIG. 5. As shown, the output 59 of the monostable 57 drives a transistor 64. The transistor 64 charges an integrating capacity 66, such that the integrating capacitor 66 has a voltage that varies with a frequency corresponding to the blood flow in the blood vessel being monitored. A resistor 68 may be provided to control the charging rate of the integrating capacitor 66.

Referring again to FIG. 3, the signal processing signal 20 may also include an analog to digital converter ("ADC") 70 to drive a display driver 72. In examples where the display driver accepts an analog signal, the ADC 70 may be optional. A display driver 72 may be provided to drive the visual display 22 with an indicator representing the flow rate through the blood vessel being monitored.

Figure 6:
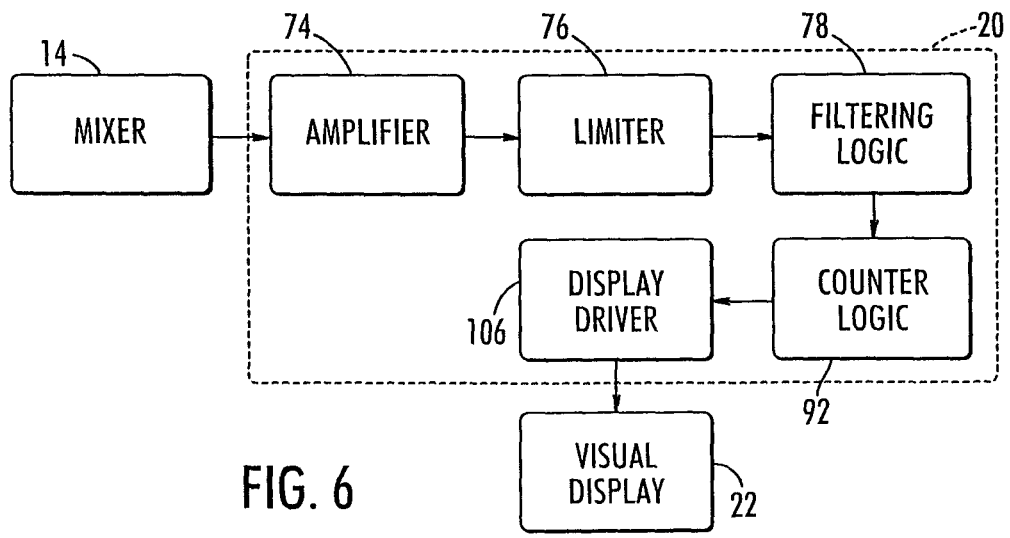
FIG. 6 is an example implementation of the signal processing circuit with a mixer and visual display.

FIG. 6 shows another implementation of the signal processing circuit 20. As shown, the signal processing circuit 20 includes an amplifier 74 for increasing the amplitude of the signal received from the mixer 14. As discussed with reference to the implementation in FIG. 3, the amplifier 74 may be a single stage or multi-stage amplifier. For example, the two stage amplifier 32 shown in FIG. 4 may be used with this implementation of the signal processing circuit 20.

The signal processing circuit 20 may include a limiter 76 for converting the analog signal received from the amplifier 74 to a signal with digital voltage levels. The limiter 46 shown in FIG. 4 may be used with the implementation of the signal processing circuit 20 shown in FIG. 6. Any other component or circuit capable of converting an analog signal to digital voltage levels, such as an analog to digital converter ("ADC") or level shifter may be used.

The signal processing circuit 20 may optionally include filtering logic 78 to reduce any high frequency noise that may be included in the signal received from the limiter 76. The filtering logic 78 may be implemented in hardware and/or software, such as using a resistor/capacitor filter or a digital filter.

Figure 7:
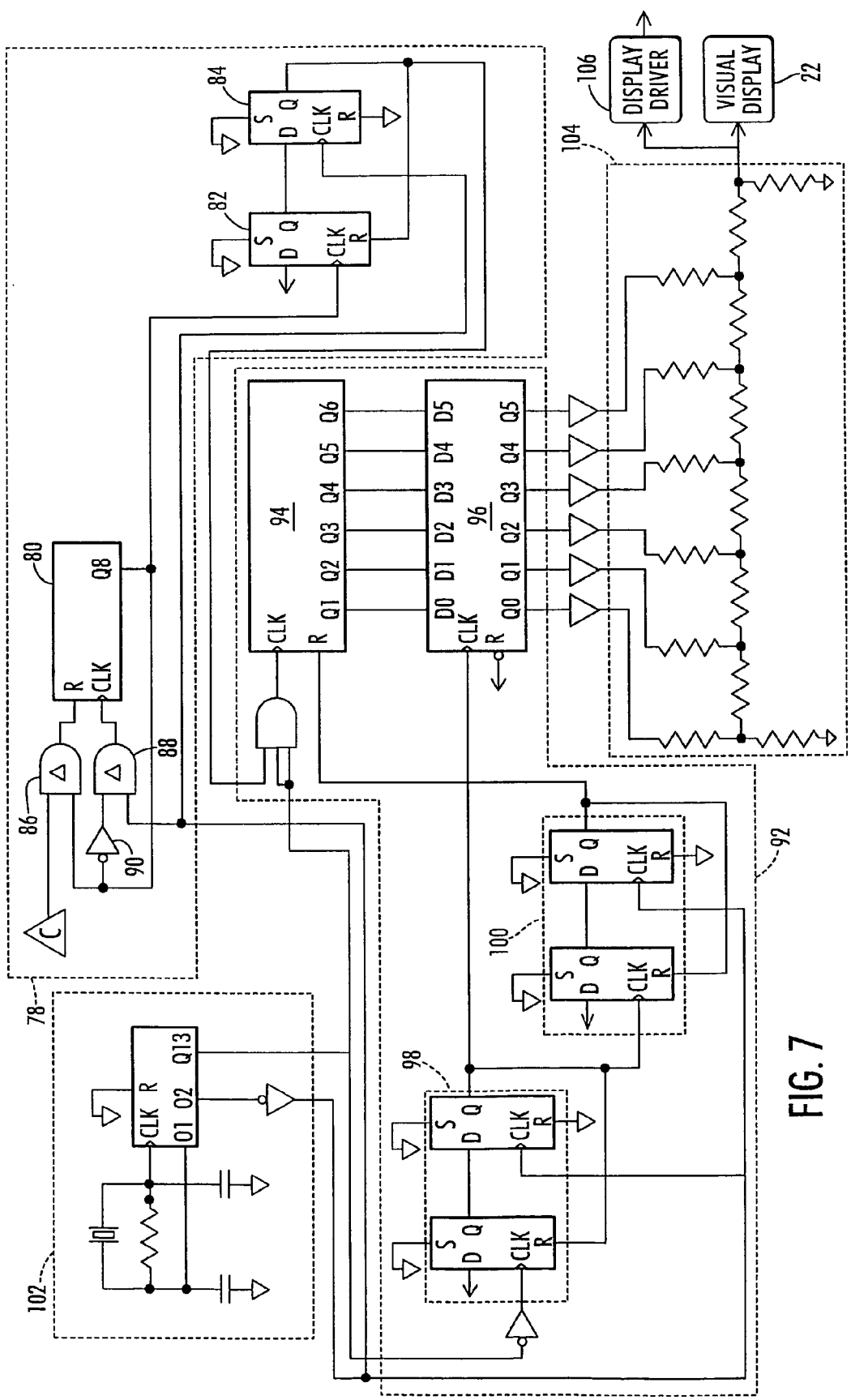
FIG. 7 is a schematic diagram of a circuit implementation of the signal processing circuit shown in FIG. 6.

An example implementation of the filtering logic 78 is shown in FIG. 7. As shown, the filtering logic 78 includes a non-retriggerable monostable 80, a first flip-flop 82, and a second flip-flop 84. The non-retriggerable monostable 80 has a reset input (R) and a clock input (CLK). The reset input is connected to an and gate 86 having a first input connected to the output of the limiter 76 (indicated by triangle with C) and a second input connected to the output (Q8) of the non-retriggerable monostable 80. The clock input of the non-retriggerable monostable 80 is connected to the output of an and gate 88. The inputs to the and gate 88, includes an inverter 90 and a sampling clock 102. The output (Q8) of the non-retriggerable monostable 80 is connected to the input of the inverter 90. The output (Q8) of the non-retriggerable monostable 80 is also connected to a clock input (CLK) of the first flip-flop 82. The output (Q) of the first flip-flop 82 is connected to the input (D) of the second flip-flop 84. The clock input (CLK) of the second flip-flop 84 connected to the sampling clock 102. When the output (Q8) of the nonretriggerable monostable 80 goes high, this triggers the first flip-flop 82, which triggers the second flip-flop 84 to go high for a period of time. Since the monostable is non-retriggerable, high frequencies received from the limiter 76 are filtered from the output of the second flip-flop 84.

Referring again to FIG. 6, the output of the filtering logic 78 is connected to the input of a counter logic 92. The counter logic 92 counts the number of rising or falling edges in the input signal during a sample period. If the blood flow through the vessel being monitored corresponded to 100 Hz, for example, the output of the counter logic 92 for a sample period of 0.25 seconds would be 25.

The length of the sample period and number of bits used in the counter logic 92 allows the full scale of the visual display 22 to be adjusted. The counter logic 92 may be configured to have a full scale reading that is less than the possible frequency associated with the maximum flow through the blood vessel being monitored. For example, if the counter logic 92 was capable of storing an 8-bit number, the maximum count for a sample period would be 256 (i.e., $2^8$). If the sample period were 0.25 seconds in this example, the counter logic 92 would be at full scale at 1024 (i.e., 256*4) Hz. In other words, the maximum output of the counter logic 92 would correspond to 1024 Hz. In this example, the full scale of the counter logic 92 may be adjusted to correspond to 512 Hz by adjusting the sample period to 0.5 seconds (i.e., $2^8*(1/0.5)$). The ability to adjust the visual display 22 to be full scale over a portion of the potential bandwidth allows the lower frequencies to be more easily monitored.

An example implementation of the counter logic 92 is shown in FIG. 7. As shown, the counter logic 92 includes a counter 94, a Hex-D flip-flop 96, latch logic 98 and reset logic 100. A sampling clock 102 is also provided as an input to the counter logic 92 to periodically update the count in the Hex-D flip-flop 96. For example, when the sampling clock 102 is high, the counter 94 will count each rising edge on the input signal received from the filtering logic 78 (output (Q) of second flip-flop 84). When the sampling clock 102 goes low, the latch logic 98 will latch the current count of the counter 94 into the Hex-D flip-flop 96. After the new count is latched, the reset logic 100 will clear the counter 94 to be ready for the next pulse of the sampling clock 102. The output of the Hex-D flip-flop 96 is provided to a ladder network 104.

The output of the ladder network 104 results in a variable voltage that corresponds to the frequency of the output from the mixer 14. In the example shown, the Hex-D flip-flop 96 has 6 bits of information. With this example, 64 (i.e., $2^6$) discrete voltage steps may be produced in the ladder network 104. If the sampling clock 102 were timed at a frequency of 4 Hz (0.25 pulses per second), for example, the full scale voltage that may be displayed on the visual display 22 would be 256 Hz (64×4). This means that the visual display 22 would be at full scale for any frequency monitored on the blood vessel above 256 Hz in this example. For frequencies below 256 Hz, in this example, the visual display will indicate in approximate frequency corresponding to the flow of blood through the vessel being monitored. A display driver 106 may receive the output of the counter logic 92. The display driver 106 may be provided to drive the visual display 22 with an indicator representing the flow rate through the blood vessel being monitored.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. A blood flow monitor for detecting a blood flow rate down to zero flow, within a single blood vessel, comprising:
    a transducer probe directly contactable on a single blood vessel, a visual display, and a speaker;
    a probe monitoring circuit in electrical communication with said probe, where the probe monitoring circuit is configured to transmit a burst signal at a predetermined first frequency and receive a reflected signal at a second frequency;
    a mixer comprising an input in electrical communication with the probe monitoring circuit and an output in electrical communication with a first signal path and a second signal path, where the mixer is configured to compare the difference between the first frequency and the second frequency to determine a frequency shift, the frequency shift representative of a blood flow rate within the single blood vessel, wherein the frequency shift has a range between zero to indicate a zero flow rate and an upper limit frequency with a threshold frequency therebetween, where the threshold frequency is a frequency that is at least audible in said speaker, the mixer further configured to output a signal at a frequency of the frequency shift to each of the first and second signal paths;
    the first signal path including the speaker in electric communication with the output of the mixer, the speaker configured to produce an audible sound in response to the frequency shift signal having a frequency between the threshold frequency and the upper limit frequency to audibly indicate said blood vessel having a blood flow rate; and
    the second signal path including a signal processing circuit comprising an input in electrical communication with the output of the mixer and an output in electrical communication with the visual display, where the signal processing circuit is configured to drive the visual display with a signal in response to the frequency shift signal having a frequency between zero and the threshold frequency to visually indicate the blood vessel having a blood flow,
    wherein the visual display is configured to provide incremental visual indication of the blood flow rate when said blood flow rate is within a range from a blood flow rate associated with said threshold frequency down to said zero flow rate.

2. The blood flow monitor as recited in claim 1, where the signal processing circuit includes an amplifier in electrical communication with the output of the mixer.

3. The blood flow monitor as recited in claim 2, where the signal processing circuit includes filtering logic configured to implement a low pass filter, so that the frequency shift signal that has a frequency between zero and the threshold frequency is unfiltered.

4. The blood flow monitor as recited in claim 3, where the amplifier includes an output and the filtering logic includes an input, where the output of the amplifier is in electrical communication with the input of the filtering logic.

5. The blood flow monitor as recited in claim 1, where the signal processing circuit includes a scaling logic configured to generate a scaled signal from the frequency shift signal having a frequency between zero and the threshold frequency, representing the blood flow rate associated with the blood vessel in the range from a blood flow rate associated with said threshold frequency down to said zero flow rate.

6. The blood flow monitor as recited in claim 5, where the scaled signal has a frequency that varies corresponding to the frequency of the frequency shift signal representative of the blood flow rate associated with the blood vessel, wherein the visual display indicates incremental changes of said blood flow as said scaled signal varies.

7. The blood flow monitor as recited in claim 1, where the visual display is selected from the group consisting of a LED bar graph, a LCD bar graph, a calibrated needle, and a numeric display.

8. The blood flow monitor as recited in claim 1, where the probe monitoring circuit includes a piezoelectric crystal, where the piezoelectric crystal transmits the burst signal at an ultrasonic frequency and receives the reflected signal.

9. The blood flow monitor as recited in claim 1, where the threshold frequency is in the range of 100 Hz to 256 Hz.

10. The blood flow monitor as recited in claim 9, where the threshold frequency is 150 Hz.

11. The blood flow monitor as recited in claim 1, where the first signal path further comprises an amplifier configured to amplify the frequency shift signal having a frequency between the threshold frequency and the upper limit frequency from the mixer sufficiently to drive the speaker, and further configured to filter noise from the frequency shift signal before being output to the speaker, the amplifier comprising an input in electrical communication with the output of the mixer and an output in electrical communication with the speaker.

12. A signal processing circuit comprising:
    an input channel configured to receive an input signal at a frequency shift define between a burst signal at a first frequency and a reflected signal at a second frequency to represent a blood flow rate through a blood vessel, wherein the frequency shift has a range between zero to indicate a zero flow rate and an upper limit frequency with a threshold frequency therebetween, wherein the threshold frequency is a frequency that is at least audible in a speaker;
    an output channel configured to output an output signal; and
    a scaling logic connected between the input channel and the output channel, where the scaling logic is configured to generate a scaled signal configured to drive a visual display that is incremental, the scaled signal indicative of the frequency shift in the range between zero and the threshold frequency in order to visually represent the blood flow rate associated with the blood vessel on the visual display when said blood flow rate is in a range from a blood flow rate associated with said threshold frequency down to said zero flow rate.

13. The signal processing circuit as recited in claim 12, where the scaled signal has a frequency that varies corresponding to the frequency of the frequency shift representative of the flow rate associated with the blood vessel, wherein the visual display visually indicates incremental changes of said blood flow rate from a minimum increment to a maximum increment as said scaled signal varies incrementally.

14. The signal processing circuit as recited in claim 13, further comprises a low pass filter so that the frequency shift signal that has a frequency between zero and the threshold frequency is unfiltered.

15. The signal processing circuit as recited in claim 12, further comprising an amplifier prior to the scaling logic, and a display driver after the scaling logic.

16. A method of monitoring a blood flow rate through a blood vessel, the method comprising:
   transmitting a burst signal at a predetermined first frequency proximate to a blood vessel;
   receiving a reflected signal at a second frequency, where a frequency shift in the reflected signal relative to the first frequency represents a blood flow rate associated with the blood vessel;
   comparing the frequency shift with a threshold frequency being capable of audio output through a speaker; and
   driving a visual display configured to provide incremental visual indication of the blood flow rate within the body vessel when the frequency shift is within a range from the threshold frequency down to zero frequency to represent a low flow rate associated with the blood vessel, and driving a speaker when the frequency shift is above the threshold frequency to represent a flow rate associated with the blood vessel higher than the indicated blood flow rate of the visual display.

17. The method as recited in claim 16, further comprising scaling the frequency shift when the frequency shift is below the threshold frequency, wherein the visual display is incremental from a minimum increment to a maximum increment, where in the driving a visual display step, the visual indication from the visual display that is less than the maximum increment represents a blood flow within a range from a blood flow rate associated with said threshold frequency down to said zero flow rate.

18. The method as recited in claim 17, wherein the driving a visual display step further occurs when the frequency shift is above the threshold frequency to indicate that the blood flow rate is higher than the indicated blood flow rate of the maximum increment of the visual display, and the driving a speaker step occurs only when the frequency shift is at or above the threshold frequency.

* * * * *